US006858746B2

(12) United States Patent
Giessler et al.

(10) Patent No.: US 6,858,746 B2
(45) Date of Patent: Feb. 22, 2005

(54) PROCESS FOR THE HYDROSILYLATION OF UNSATURATED ALIPHATIC COMPOUNDS

(75) Inventors: Sabine Giessler, Rheinfelden (DE); Helmut Mack, Rheinfelden (DE); Dieter Barfurth, Rheinfelden (DE)

(73) Assignee: Degussa AG, Duesseldorf (DE)

(*) Notice: Subject to any disclaimer, the term of this patent is extended or adjusted under 35 U.S.C. 154(b) by 185 days.

(21) Appl. No.: 10/267,819

(22) Filed: Oct. 10, 2002

(65) Prior Publication Data

US 2003/0100784 A1 May 29, 2003

(30) Foreign Application Priority Data

Oct. 10, 2001 (DE) .......................................... 101 49 967
Sep. 18, 2002 (DE) .......................................... 102 43 180

(51) Int. Cl.$^7$ ................................................. C07F 7/08
(52) U.S. Cl. ...................... 556/481; 556/445; 556/415
(58) Field of Search ................................ 556/481, 445, 556/415

(56) References Cited

U.S. PATENT DOCUMENTS 3,775,452 A    11/1973   Karstedt et al.

6,251,057 B1 * 6/2001 Jung et al. .................. 556/481

FOREIGN PATENT DOCUMENTS

| DE | 1 941 411 | 12/1970 |
| EP | 0 263 673 | 4/1988 |
| EP | 0 573 282 | 12/1992 |
| EP | 0 838 467 | 4/1998 |

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A compound having at least one H—Si group is reacted with an unsaturated aliphatic compound in the presence of a platinum catalyst and at least one organic additive component. The combination of platinum catalyst and additive component is one of:

(i) a solution of a Pt(0) complex catalyst in a solvent, with at least one organic amide, or
(ii) a solution of a Pt(0) complex catalyst in a solvent, with at least one organic amine, or
(iii) a solution of a Pt(0) complex catalyst, in a solvent, with at least one organic nitrite.

22 Claims, No Drawings

PROCESS FOR THE HYDROSILYLATION OF UNSATURATED ALIPHATIC COMPOUNDS

BACKGROUND OF THE INVENTION

1. Field of the Invention

The present invention is a process for preparing organofunctional organosilicon compounds by reacting olefins with a compound containing H—Si groups in the presence of a dissolved platinum catalyst and at least one further additive component.

2. Discussion of the Background

Organofunctional silanes are of great economic interest and are now employed in many industrial applications. 3-Chloropropylchlorosilanes in particular are important intermediates in the preparation of organofunctional silanes. They are generally prepared by the hydrosilylation of allyl chloride. For example, 3-chloropropyltrichlorosilane and 3-chloropropylmethyldichlorosilane can be used to prepare, for example, 3-chloropropyltrialkoxysilanes, 3-chloropropylmethyldialkoxysilanes, 3-aminopropyltrialkoxysilanes, 3-aminopropylmethyldialkoxysilanes, N-aminoethyl-3-aminopropyltrialkoxysilanes, N-aminoethyl-3-aminopropylmethyldialkoxysilanes, 3-cyanopropylalkoxysilanes, 3-glycidyloxypropylalkoxysilanes, 3-methacryloxypropylalkoxysilanes, to name only a few examples.

The addition of Si—H groups onto aliphatic multiple bonds has been known for a long time, and is known as hydrosilylation. This reaction is promoted by, for example, homogeneous and heterogeneous platinum catalysts. Examples of heterogeneous platinum catalysts include, for example, platinum metal, in particular finely divided platinum on a support such as activated carbon. Homogeneous platinum catalysts include, for example, hexachloroplatinic acid, alcohol-modified hexachloroplatinic acid, olefin complexes of hexachloroplatinic acid or vinylsiloxane complexes of hexachloroplatinic acid or of platinum. Complexing reagents are frequently added to a catalyst system to increase selectivity and reactivity, which in some cases also improves the solubility of the platinum compound.

EP 0 573 282 A1 discloses the use of $H_2PtCl_6$ in 2-ethylhexanal and also addition of m-xylene hexafluoride.

EP 0 263 673 A2 teaches the preparation of 3-chloropropyltrichlorosilane by hydrosilylation using hexachloroplatinic acid dissolved in isopropanol (Speier catalyst), and the addition of N,N-dimethylacetamide.

The hydrosilylation of allyl chloride and methyldichlorosilane in the presence of the Speier catalyst system generally forms two undesirable by-products: chloropropylmethylchloropropoxysilane and dichloromethylpropoxysilane. Chloropropylmethylchloropropoxysilane can be separated from the target product chloropropylmethyldichlorosilane (CPMDCS) only with great difficulty.

There are many examples of metal complex catalysts added to reactions for the purpose of positively influencing homogeneously catalyzed reactions.

Karstedt catalysts (Pt(0) complexes) have also been used for hydrosilylations since 1973. Thus, for example, DE-A 19 41 411 and U.S. Pat. No. 3,775,452 disclose platinum catalysts of the Karstedt type. This type of catalyst generally has a high stability, especially in an oxidizing matrix, a high effectiveness and a low tendency to isomerize carbon frameworks.

EP 0 838 467 A1 discloses a process for preparing silanes having fluoroalkyl groups using a Pt(0) complex catalyst which is dissolved in xylene.

Experiments show that the hydrosilylation of, for example, allyl chloride with methyldichlorosilane at a molar ratio of 1:1 in the presence of a Karstedt catalyst such as CPC072® gives a yield of 3-chloropropylmethyldichlorosilane of not more than 49 mol %.

SUMMARY OF THE INVENTION

It is an object of the present invention to provide a novel process for the addition of a compound containing at least one H—Si group onto an unsaturated aliphatic compound in the presence of a platinum catalyst. A particular aim of the present invention is to provide an improved process for preparing 3-chloropropylchlorosilanes. This object is achieved as discussed below. It has surprisingly been found that Pt(0) complex catalysts, e.g., Karstedt catalysts such as CPC072®, with the addition of at least one organic amide, amine or nitrile reduce the amount of undesirable secondary reactions occurring compared to previously known catalysts in combination with specific additive components.

For example, a secondary reaction such as the formation of propene from allyl chloride, which can then react, for example, with methyldichlorosilane to form the undesired propylmethyldichlorosilane, can be reduced in this way. Thus, the surprisingly advantageous action of the combination of a Pt(0) complex catalyst dissolved in a solvent with an amide, an amine or a nitrile, hereinafter also referred to as catalyst system, provides, in a simple and economical way, a novel process for the addition of a compound containing at least one H—Si group onto an unsaturated aliphatic compound. In addition, the formation of a by-product such as chloropropylmethylchloropropoxysilane which is difficult to distill off from the desired product, can be suppressed.

DETAILED DESCRIPTION OF THE INVENTION

The present invention accordingly provides a process for the addition of a compound containing at least one H—Si group (i.e., a hydrosilane) onto an unsaturated aliphatic compound by reacting the unsaturated aliphatic compound with the hydrosilane in the presence of a platinum catalyst and at least one organic additive component. More specifically, the reaction is carried out in the presence of:
(i) a solution of a Pt(0) complex catalyst and at least one organic amide in a solvent, or
(ii) a solution of a Pt(0) complex catalyst and at least one organic amine in a solvent, or
(iii) a solution of a Pt(0) complex catalyst and at least one organic nitrile in a solvent.

In the process of the present invention, the reaction is preferably carried out using at least one unsaturated aliphatic compound of the formula I

X—(CH$_2$)$_n$—C(R$^1$)=CH$_2$         (I), where X is a hydrogen atom, chlorine, bromine or cyano or nitrile (—CN), a fluoroalkyl group of the formula $C_mF_{2m+1}$, where m=1 to 20, an alkoxy polyether of the formula $R^1O$—$(CH_2$—$CHR^1$—$O)_y$—, where y=0 to 30, 2,3-epoxy-1-propyl or CH$_2$=CR—COO—, where the groups $R^1$ are identical or different and $R^1$ is a hydrogen atom or a linear or branched $C_1$–$C_4$-alkyl group and n is an integer from 0 to 3.

3-Chloro-1-propene, also referred to as allyl chloride, or 3-chloro-2-methyl-1-propene, also known as methallyl chloride, are particularly preferred examples pf an unsaturated aliphatic compound.

Hydrosilane compounds of formula II are preferred:

$$H_{(4-a-b)}SiR_aY_b \qquad (II),$$

where the groups R are identical or different and R is a linear, branched or cyclic alkyl group having from 1 to 16 carbon atoms or an aryl group, the groups Y are identical or different and Y is chlorine, bromine, methoxy, or ethoxy, and a is an integer from 0 to 3 and b is an integer from 0 to 3, with the proviso that $1 \leq (a+b) \leq 3$.

Trichlorosilane, methyldichlorosilane or dimethylchlorosilane are preferred hydrosilanes.

The unsaturated aliphatic compound and the hydrosilane are advantageously reacted in a molar ratio of from 20:1 to 1:5, particularly preferably from 10:1 to 1:3, very particularly preferably from 8:1 to 1:2.

Furthermore, a Pt(0) complex catalyst of the Karstedt type is used in the process of the present invention. The Pt(0) complex is advantageously a catalyst containing from 0.01 to 20% by weight of platinum, preferably from 0.1 to 10% by weight of platinum, particularly preferably from 0.5 to 5% by weight of platinum. The Karstedt catalyst, i.e. a Pt(0) complex, is particularly preferably the platinum(0)-divinyltetramethyldisiloxane complex or platinum(0)-divinyltetramethyldisiloxane complex of the formula $Pt_2\{[(CH_2=CH)(CH_3)_2Si]_2O\}_3$, which is commercially available, for example, in the form of a 5% strength solution in xylene under the name "CPC072®".

The Pt(0) complex catalyst may be a solution in a largely inert, aromatic hydrocarbon solvent, preferably xylene or toluene, in a ketone solvent, preferably acetone, methyl ethyl ketone or cyclohexanone, or in an alcohol solvent, preferably methanol, ethanol, n- or i-propanol. The Pt(0) content of the solution is, in particular, from 0.1 to 10% by weight, preferably from 0.5 to 5% by weight, particularly preferably from 1 to 3% by weight, very particularly preferably 2% by weight.

Furthermore, the Pt(0) complex catalyst system, i.e., Pt(0) and the unsaturated aliphatic compound, are present in the process of the present invention in a molar ratio of from 1:1000 to 1:70000, particularly preferably from 1:10000 to 1:60000, very particularly preferably from 1:15000 to 1:40000.

The organic amide additive component of the present invention preferably has the formula III:

$$R^2-CONR^3R^4 \qquad (III),$$

where $R^2$ may be a hydrogen or a linear, branched or cyclic alkyl group having from 1 to 16 carbon atoms, preferably methyl or ethyl, or an aryl or an alkenyl group having from 2 to 8 carbon atoms, preferably vinyl, allyl (=3-propen-1-yl) or methallyl (=2-methyl-3-propen-1-yl), or an aryl group, preferably phenyl or tolyl, and the groups $R^3$ and $R^4$ are identical or different and each may be a hydrogen atom or a linear, branched or cyclic alkyl group having from 1 to 8 carbon atoms, preferably hydrogen, methyl, or ethyl, or an aryl group or an alkenyl group having from 2 to 8 carbon atoms. N,N-Dimethylacetamide (DMA) or N,N-dimethylformamide (DMF) are preferred as the amide component in the process of the present invention.

In carrying out the process of the present invention, it is possible, for example, to first add an organic amide to the Pt(0) base complex catalyst solution and subsequently to add the amide-containing catalyst solution to the mixture of a hydrosilane and at least one unsaturated aliphatic compound. However, it is also possible for the solution of Pt(0) catalyst and solvent to be added initially to one of the two starting components (i.e., the hydrosilane and unsaturated aliphatic compound), or a mixture thereof, and then the amide may subsequently be added, preferably with good mixing. In addition, it is possible for the amide to be initially added to one of the two starting components, or a mixture thereof, and then the Pt(0) catalyst solution may be subsequently added into the reaction mixture. It is likewise possible to meter one of the starting components, preferably the hydrosilane, into the reaction mixture.

In general, the process of the present invention may be carried out in the same way as described above for the organic amide additive component, by reacting the starting components in the presence of the Pt(0) complex catalyst in combination with a compound of the formula (IV) or (V), below. Thus, the present reaction can be carried out using at least one organic amine additive component of formula IV

$$R^5-NR^6R^7 \qquad (IV),$$

where the groups $R^5$, $R^6$ and $R^7$ are identical or different and each may be a hydrogen atom or a linear, branched or cyclic alkyl group having from 1 to 8 carbon atoms or an alkenyl group having from 2 to 8 carbon atoms or an aryl group.

The organic amine is preferably N,N-dimethylbutylamine, tert-butylamine or triethylamine.

Furthermore, the present reaction can be carried out using at least one organic nitrile additive component of formula V

$$R^8-CN \qquad (V),$$

where $R^8$ is a linear, branched or cyclic alkyl group having from 1 to 16 carbon atoms.

A preferred organic nitrile is butyronitrile.

The additive component of the formula (III), (IV) or (V) and the Pt(0) complex catalyst preferably have a molar ratio of from 10:1 to 1:10; particular preferably a molar ratio of 1:1.

Furthermore, the platinum in the catalyst and the hydrosilane of formula II have a molar ratio of from $1:10^{10}$ to $1:10^2$, particularly preferably from $1:10^8$ to $1:10^3$.

The process of the present invention is usually carried out at a temperature in the range of from 10 to 200° C., preferably from 20 to 200° C., particularly preferably from 30 to 150° C. Furthermore, the process of the present invention is carried out at a pressure in the range from 1 to 50 bar absolute, preferably from 1 to 10 bar absolute, in particular at the pressure of the surrounding atmosphere (approximately 1 bar absolute).

Functional organosilanes may be prepared by the process of the present invention. For example, the functional organosilanes may be 3-chloropropyltrichlorosilane, 3-chloropropyltrialkoxysilanes, 3-chloropropylmethyldichlorosilane and 3-chloropropylmethyldialkoxysilanes, where the alkoxy group is preferably methoxy or ethoxy.

The preferred reactants in the process of the present invention are 3-chloro-1-propene reacted with a hydrochlorosilane of formula II, in particular with trichlorosilane or methyldichlorosilane. The reactants are reacted in the presence of a platinum(0) complex catalyst and in addition with at least one organic amide, nitrile or amine. The catalyst and the amide, the nitrile or amine are preferably mixed together as a solution in a solvent. The resulting hydrosilylation product formed in the reaction mixture may then be esterified in a known manner with an alcohol to give a 3-chloropropylalkoxysilane. Preferred alcohols for the esterification of the hydrosilylation product may be, for example, methanol, ethanol or 2-methoxyethanol.

In general, the process of the present invention may be carried out as follows:

For example, the unsaturated aliphatic component, e.g. allyl chloride, is first placed in a reaction vessel. The hydrosilane, e.g. methyldichlorosilane, is subsequently added to the unsaturated aliphatic component and the contents of the reaction vessel are mixed well. The platinum(0) complex catalyst system, which has been prepared separately by mixing the platinum complex, e.g. CPC072, with the additive component, e.g. dimethylformamide, is then added. The reaction mixture may then be slowly heated until the boiling point of the mixture has been reached and reflux commences. The boiling temperature is determined by the identity of the reaction components (starting materials).

The occurrence of the hydrosilylation reaction is generally indicated by an increase in the liquid-phase temperature in the reaction vessel, because the addition reaction forms products which have boiling points which are significantly higher than those of the starting materials. The conversion of the starting materials is generally monitored by regular sampling and GC analysis of the constituents. As soon as no appreciable increase in the amount of the desired reaction product in the reaction mixture is observed, the low-boiling constituents of the reaction mixture may be distilled off, if appropriate, under reduced pressure. A distillation of the product may subsequently be carried out, also under reduced pressure, if necessary, to further purify the product.

As a result of the excellent activity of the catalyst system of the present invention, the addition of the hydrosilane to the unsaturated aliphatic compound generally takes place so quickly that secondary reactions are largely suppressed and the yield and purity of the desired product is significantly higher than would be the case if a catalyst of the prior art is used. Thus, for example, 3-chloropropyltrichlorosilane can be prepared in excellent yield in an advantageous manner, i.e. simply and economically, by the process of the present invention.

Having generally described this invention, a further understanding can be obtained by reference to certain specific examples which are provided herein for purposes of illustration only, and are not intended to be limiting unless otherwise specified.

EXAMPLES

Comparative Example A

In a 500 ml four-necked glass flask provided with water-cooled condenser, low-temperature condenser, stirrer, thermometer and dropping funnel, 76.5 g (1.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, molar ratio of Pt to methyldichlorosilane= 1:30000) were added to this mixture. The reaction mixture was subsequently heated to about 42–43° C. The mixture then began to boil. As a result of the addition reaction, the content of relatively high-boiling reaction product increased, and the temperature of the reaction mixture reached about 93° C. Samples were taken during the reaction and analyzed by gas chromatography. After a reaction time of about 4 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 55 to 65° C. and at atmospheric pressure, the desired product (i.e., chloropropylmethyldichlorosilane) was distilled from the reaction mixture at a temperature of about 85° C. at the top of the distillation apparatus and at a pressure of 20 mbar. This procedure provided 93.3 g of product (49% of the theoretical yield) having a purity of 98 GC-% (by area). The selectivity was 50%.

Comparative Example B

In a 500 ml three-necked glass flask provided with water-cooled condenser, low-temperature condenser, stirrer, thermometer and dropping funnel, 153.1 g (2.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, molar ratio of Pt to methyldichlorosilane= 1:30000) were added to this mixture. The reaction mixture was subsequently heated to about 42–43° C. The mixture then began to boil. As a result of the addition reaction, the content of relatively high-boiling reaction product increased and the temperature of the reaction mixture reached about 52° C. Samples were taken during the reaction and analyzed by gas chromatography. After a reaction time of about 4.5 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 55 to 65° C. and at atmospheric pressure, the desired product (i.e., chloropropylmethyldichlorosilane) was distilled from the reaction mixture at 71–73° C. and 23 mbar. This procedure provided 92.1 g of product (48.1% of the theoretical yield) having a purity of 97.6 GC-% (by area).

Comparative Example C

In a 500 ml four-necked glass flask provided with water-cooled condenser, low-temperature condenser, stirrer, thermometer and dropping funnel, 76.5 g (1.0 mol) of allyl chloride and 115.0 g (1.0 mol) of methyldichlorosilane were mixed under a nitrogen atmosphere. At room temperature, 0.87 g of hexachloroplatinic acid dissolved in isopropanol (molar ratio of Pt to methyldichlorosilane=1:30000) was added to this mixture. The reaction mixture was subsequently heated to about 42–43° C. The mixture then began to boil. As a result of the addition reaction, the content of relatively high-boiling reaction product increased and the temperature of the reaction mixture reached about 95° C. Samples were taken during the reaction and analyzed by gas chromatography. After a reaction time of about 4 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 55 to 65° C. and at atmospheric pressure, the desired product (i.e., chloropropylmethyldichlorosilane) was distilled from the reaction mixture at about 85° C. and 19 mbar. This procedure provided 91.3 g of product (48% of the theoretical yield) having a purity of 91.2 GC-% (by area). The selectivity was 49%. Two undesirable by-products (chloropropylmethylchloropropoxysilane and dichloromethylpropoxysilane) were formed in the hydrosilylation of allyl chloride using the Speier catalyst system. The former may be separated from the desired product only with difficulty. It was present in the product fraction in an amount of 1.16 GC-% (by area).

Example 1

In a 500 ml three-necked glass flask provided with water-cooled condenser, stirrer, thermometer and dropping funnel, 114.8 g (1.5 mol) of allyl chloride and 172.5 g (1.5 mol) of methyldichlorosilane were mixed under a nitrogen atmosphere. At room temperature, 0.48 g of CPC072® (Pt(0)-divinyltetramethyldisiloxane in xylene, 2% of Pt, modified with 1 mol of N,N-dimethylacetamide per mole of Pt; molar ratio of Pt to methyldichlorosilane=1:30000) was added to this mixture. The reaction mixture was subsequently heated to about 44–46° C. The mixture then began to boil. As a result of the addition reaction, the content of relatively high-boiling reaction product increased and the temperature of the reaction mixture reached about 107° C. after 2 hours. Samples were taken during the reaction and analyzed by gas chromatography. After a reaction time of about 4 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 50 to 55° C. and at atmospheric pressure, the desired product (i.e., chloropropylmethyldichlorosilane) was distilled from the reaction mixture at 68–70° C. and 20 mbar. This procedure provided 233.6 g of product (81.1% of the theoretical yield) having a purity of 97.9 GC-% (by area).

Example 2

In a 500 ml three-necked glass flask provided with water-cooled condenser, stirrer, thermometer and dropping funnel, 153.1 g (2.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, modified with 1 mol of N,N-dimethylacetamide per mole of Pt; molar ratio of Pt to methyldichlorosilane=1:30000) was added to this mixture. The reaction mixture was subsequently heated to about 44–46° C. The mixture then began to boil. The addition reaction commenced, and the temperature of the reaction mixture reached about 49° C. after 6 hours. Samples were taken during the reaction and analyzed by gas chromatography. After a reaction time of about 7 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 55 to 60° C. and at atmospheric pressure, the desired product (i.e., chloropropylmethyldichlorosilane) was distilled from the reaction mixture at 71–74° C. and 22 mbar. This procedure provided 159.6 g of product (83.3% of the theoretical yield) having a purity of 98.7 GC-% (by area).

Example 3

In a 500 ml three-necked glass flask provided with water-cooled condenser, stirrer, thermometer and dropping funnel, 114.8 g (1.5 mol) of allyl chloride and 172.5 g (1.5 mol) of methyldichlorosilane were mixed under a nitrogen atmosphere. At room temperature, 0.48 g of CPC072® (Pt(0)-divinyltetramethyldisiloxane in xylene, 2% of Pt, modified with 1 mol of N,N-dimethylformamide per mole of Pt; molar ratio of Pt to methyldichlorosilane=1:30000) was added to this mixture. The reaction mixture was subsequently heated to about 44–46° C. The mixture then began to boil. As a result of the addition reaction, the content of relatively high-boiling reaction product increased and the temperature of the reaction mixture reached about 91° C. after 90 minutes. Samples were taken during the reaction and analyzed by gas chromatography. After a reaction time of about 3.5 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 50 to 60° C. and at atmospheric pressure, the desired product (i.e., chloropropylmethyldichlorosilane) was distilled from the reaction mixture at 75–77° C. and 25 mbar. This procedure provided 220.1 g of product (76.6% of the theoretical yield) having a purity of 98.1 GC-% (by area).

Example 4

In a 500 ml four-necked glass flask provided with water-cooled condenser, low-temperature condenser, stirrer, thermometer and dropping funnel, 76.5 g (1.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, modified with 1 mol of butyronitrile per mole of Pt; molar ratio of Pt to methyldichlorosilane= 1:30000) was added to this mixture. The reaction mixture was subsequently heated to about 42–45° C. The mixture then began to boil. The addition reaction commenced and the temperature of the reaction mixture reached about 75° C. after 4 hours. Samples were taken during the reaction and analyzed by gas chromatography. After a reaction time of about 4.5 hours, the reaction was complete: the amount of reaction product (chloropropylmethyldichlorosilane) was constant. The reaction mixture was worked up by distillation via a distillation bridge. After the low boilers (unreacted starting materials) were separated off at from 55 to 62° C. and atmospheric pressure, the desired product (i.e., chloropropylmethyldichlorosilane) was distilled from the reaction mixture at about 74° C. and 35 mbar and was obtained in a GC purity of 96.38%. 118.4 g of product were obtained (62% of the theoretical yield).

Example 5

In a 500 ml four-necked glass flask provided with water-cooled condenser, low-temperature condenser, stirrer, thermometer and dropping funnel, 76.5 g (1.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, modified with 1 mol of N,N-dimethylbutylamine (BA) per mole of Pt; molar ratio of Pt to methyldichlorosilane=1:30000) was added to this mixture. The reaction mixture was subsequently heated to about 42–45° C. The mixture then began to boil. The addition reaction commenced and the temperature of the reaction mixture reached about 92° C. after 5 hours. Samples were taken during the reaction and analyzed by gas chromatography. After a reaction time of about 6 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 55 to 60° C. and at atmospheric pressure, the desired product (i.e., chloropropylmethyldichlorosilane) was distilled from the reaction mixture. This procedure provided 146.5 g of product (77% of the theoretical yield) having a purity of 98.7 GC-% (by area).

Example 6

In a 500 ml four-necked glass flask provided with water-cooled condenser, low-temperature condenser, stirrer, thermometer and dropping funnel, 153.0 g (2.0 mol) of allyl chloride and 115.0 g (1.0 mol) of methyldichlorosilane were mixed under a nitrogen atmosphere. At room temperature, 0.32 g of CPC072® (Pt(0)-divinyltetramethyldisiloxane in xylene, 2% of Pt, modified with 1 mol of N,N-dimethylbutylamine per mole of Pt; molar ratio of Pt to methyldichlorosilane=1:30000) was added to this mixture. The reaction mixture was subsequently heated to about 42–45° C. The mixture then began to boil. The addition reaction commenced and the temperature of the reaction mixture reached about 64° C. after 6.5 hours. Samples were taken during the reaction and analyzed by gas chromatography. After a reaction time of about 7 hours, the reaction was complete: the amount of reaction product (chloropropylmethyldichlorosilane) was constant. The reaction mixture was worked up by distillation via a distillation bridge. After the low boilers (unreacted starting materials) were separated off at a temperature of from 50 to 55° C. and at atmospheric pressure, the desired product (i.e., chloropropylmethyldichlorosilane) was distilled from the reaction mixture at a temperature of about 60° C. at the top and a pressure of 25 mbar. This procedure provided 148.4 g of product (78% of the theoretical yield) having a purity of 98.5 GC-% (by area).

| Abbreviations: | |
|---|---|
| CPMDCS | 3-chloropropylmethyldichlorosilane |
| MTCS | methyltrichlorosilane |
| MHDCS | methyldichlorosilane |
| AC | allyl chloride |
| BN | butyronitrile |
| BA | butylamine |
| DMA | N,N-dimethylacetamide |
| DMF | N,N-dimethylformamide | process of the present invention. In particular, in the preparation of 3-chloropropyltrichlorosilane from trichlorosilane according to the present invention or the preparation of 3-chloropropylmethyldichlorosilane from methyldichlorosilane according to the present invention, the formation of methyltrichlorosilane in a competing reaction is greatly reduced.

The priority documents of the present application, German applications DE 10149967.1, filed Oct. 109, 2002, and DE 10243180.9, filed Sep. 18, 2002, are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed as new and is intended to be secured by Letters Patent is:

1. A process comprising reacting a compound having at least one H—Si group with an unsaturated aliphatic compound in the presence of a solution of a platinum catalyst and at least one organic additive component selected from the group consisting of an organic amide, an organic amine, and an organic nitrile, thereby forming a hydrosilation product.

2. The process of claim 1, wherein the unsaturated aliphatic compound has a formula I:

$$X—(CH_2)_n—C(R^1)=CH_2 \qquad (I),$$

wherein X is a hydrogen atom, chlorine, bromine or cyano group (—CN), a fluoroalkyl of the formula $C_mF_{2m+1}$, where m=1 to 20, an alkoxy polyether of the formula $R^1O—(CH_2—CHR^1—O)_y—$, where y=0 to 30, 2,3-epoxy-1-propyl or $CH_2=CR—COO—$, where the groups $R^1$ are identical or different and $R^1$ is a hydrogen atom or a linear or branched $C_1$–$C_4$-alkyl group and n is an integer from 0 to 3.

3. The process of claim 1, wherein the unsaturated aliphatic compound is 3-chloro-1-propene or 3-chloro-2-methyl-1-propene.

4. The process of claim 1, wherein the compound having an H—Si group has a formula II:

$$H_{(4-a-b)}SiR_aY_b \qquad (II),$$

wherein the groups R are identical or different and R is a linear, branched or cyclic alkyl group having from 1 to Table of Experimental Results

| Example | Molar ratio of MHDCS to AC | Catalyst/Additive | Conversion of CPMDCS [mol %] | Purity of CPMDCS | Molar ratio of CPMDCS to MTCS* |
|---|---|---|---|---|---|
| A (comparative) | 1:1 | CPC072/— | 49.0 | 98.0 GC % | 1:0.75 |
| B (comparative) | 1:2 | CPC072/— | 48.1 | 97.6 GC % | 1:0.99 |
| C (comparative) | 1:1 | Speier/— | 48.0 | 91.2 GC % | 1:0.69 |
| 1 | 1:1 | CPC072/DMA | 81.1 | 97.9 GC % | 1:0.16 |
| 2 | 1:2 | CPC072/DMA | 83.3 | 98.7 GC % | 1:0.23 |
| 3 | 1:1 | CPC072/DMF | 76.6 | 98.1 GC % | 1:0.26 |
| 4 | 1:1 | CPC072/BN | 62.0 | 96.4 GC % | 1:0.37 |
| 5 | 1:1 | CPC072/BA | 77.0 | 98.7 GC % | 1:0.21 |
| 6 | 1:2 | CPC072/BA | 78.0 | 98.5 GC % | 1:0.22 |

*in the mixture after the reaction is complete

The data in the table show that the yield of hydrosilylation product may be drastically improved by carrying out the 16 carbon atoms or an aryl group, the groups Y are identical or different and Y is chlorine or bromine or methoxy or ethoxy and a is an integer from 0 to 3 and b is an integer from 0 to 3, with the proviso that $1 \leq (a+b) \leq 3$.

5. The process of claim 1, wherein the compound having an H—Si group is trichlorosilane, methyldichlorosilane or dimethylchlorosilane.

6. The process of claim 1, wherein the unsaturated aliphatic compound and the compound containing an H—Si group are mixed in a molar ratio of from 20:1 to 1:5 prior to said reacting.

7. The process of claim 1, wherein the platinum catalyst is a Pt(0) complex catalyst.

8. The process of claim 7, wherein the Pt(0) complex catalyst is a platinum(0)-divinyltetramethyldisiloxane complex or platinum(0)-divinyltetramethyldisiloxane of the formula $Pt_2\{[(CH_2=CH)(CH_3)_2Si]_2O\}_3$.

9. The process of claim 1, wherein the Pt(0) complex catalyst is a solution in an aromatic hydrocarbon, in a ketone, or in an alcohol, and the Pt(0) content of the solution is from 0.1 to 10% by weight.

10. The process of claim 1, wherein the organic additive is at least one organic amide having a formula III:

$$R^2\text{—}CONR^3R^4 \qquad (III),$$

wherein $R^2$ is hydrogen or a linear, branched or cyclic alkyl group having from 1 to 16 carbon atoms or an aryl or an alkenyl group having from 2 to 8 carbon atoms or an aryl group, and the groups $R^3$ and $R^4$ are identical or different and are each a hydrogen atom or a linear, branched or cyclic alkyl group having from 1 to 8 carbon atoms or an aryl group or an alkenyl group having from 2 to 8 carbon atoms.

11. The process of claim 1, wherein the organic amide is dimethylformamide or dimethylacetamide.

12. The process of claim 1, wherein the organic additive is at least one organic amine having a formula IV $$R^5\text{—}NR^6R^7 \qquad (IV),$$

wherein the groups $R^5$, $R^6$ and $R^7$ are identical or different and each is hydrogen atom or a linear, branched or cyclic alkyl group having from 1 to 8 carbon atoms or an alkenyl group having from 2 to 8 carbon atoms or an aryl group.

13. The process of claim 1, wherein the organic amine is tert-butylamine, N,N-dimethylbutylamine or triethylamine.

14. The process of claim 1 wherein the organic additive is at least one organic nitrile having a formula V $$R^8\text{—}CN \qquad (V),$$

wherein $R^8$ is a linear, branched or cyclic alkyl group having from 1 to 16 carbon atoms.

15. The process of claim 1, wherein the organic nitrile is butyronitrile.

16. The process of claim 7, wherein the organic additive component and the platinum of the Pt(0) complex catalyst have a molar ratio of from 10:1 to 1:10.

17. The process of claim 1, wherein the organic additive component is added to the platinum catalyst solution and the platinum catalyst solution is subsequently added to a mixture of the compound having at least one H—Si group and the at least one unsaturated aliphatic compound.

18. The process of claim 4, wherein the platinum catalyst solution and the compound having at least one H—Si group of formula II are mixed in a molar ratio (moles of platinum metal in the catalyst to moles of compound having at least one H—Si group) of from $1:10^{10}$ to $1:10^2$ prior to said reacting.

19. The process of claim 1, wherein said reacting is carried out at a temperature of from 10 to 200° C.

20. The process of claim 1, wherein said reacting is carried out at a pressure of from 1 to 50 bar absolute.

21. The process of claim 4, wherein the unsaturated aliphatic compound is 3-chloro-1-propene, Y is chlorine, the platinum catalyst is a Pt(0) complex catalyst, and the hydrosilation product is isolated and esterified with an alcohol.

22. The process of claim 21, wherein the alcohol is methanol, ethanol or 2-methoxyethanol.

* * * * *